US006766257B2

(12) United States Patent
Gupta et al.

(10) Patent No.: US 6,766,257 B2
(45) Date of Patent: Jul. 20, 2004

(54) PORE STRUCTURE ANALYSIS OF INDIVIDUAL LAYERS OF MULTI-LAYERED COMPOSITE POROUS MATERIALS

(75) Inventors: Krishna M. Gupta, Ithaca, NY (US); Nalina Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 102 days.

(21) Appl. No.: 10/041,189

(22) Filed: Jan. 8, 2002

(65) Prior Publication Data

US 2002/0147551 A1 Oct. 10, 2002

Related U.S. Application Data

(60) Provisional application No. 60/265,470, filed on Jan. 31, 2001.

(51) Int. Cl.[7] .............................................. G01N 31/00
(52) U.S. Cl. ...................................................... 702/27
(58) Field of Search .......................... 702/27; 524/496; 428/304; 423/448; 427/248; 502/402; G01N 15/08

(56) References Cited

U.S. PATENT DOCUMENTS

| 4,217,336 | A | * | 8/1980 | Maire et al. | 423/448 |
| 4,576,927 | A | * | 3/1986 | Kuroda et al. | 502/402 |
| 4,744,240 | A | | 5/1988 | Reichelt | 73/38 |
| 5,695,818 | A | * | 12/1997 | Soffer et al. | 427/248.1 |
| 5,696,198 | A | * | 12/1997 | Chereisky et al. | 524/496 |
| 5,955,185 | A | * | 9/1999 | Yoshino et al. | 428/304.4 |

FOREIGN PATENT DOCUMENTS

| DE | 1927171 | 12/1970 | G01N/13/04 |
| DE | 3312729 A1 | 10/1984 | G01N/15/08 |
| DE | 198 58 338 C 1 | * 7/2000 | G01N/15/08 |
| EP | 0139202 | 5/1985 | G01N/15/08 |
| EP | 0831318 | 3/1998 | G01N/15/08 |

OTHER PUBLICATIONS

Jena, Akshaya K. and Gupta, Krishna M.. "In–Plane Compression Porometry of Battery Separators." Journal of Power Sources 80. 1999. p. 46–52.

Gupta, Vibhor and Jena, A.K.. "Substitution of Alcohol in Porometers For Bubble Point Determination." Advances in Filtration and Separation Technology. Col. 13b, 1999 p. 833–844.

Gupta, Nalini and Jena, Akshaya. "Measuring in Layers: Determining the Pore Structure of Individual Layers of Multi–Layered Ceramic Composites." Ceramic Industry, Feb. 2001. p. 28–33.

* cited by examiner

*Primary Examiner*—John Barlow
*Assistant Examiner*—Tung Lau
(74) *Attorney, Agent, or Firm*—Brown & Michaels, PC

(57) ABSTRACT

A method of determining the pore structure of the individual layers in a multi-layered composite porous material includes the steps of providing a sample of a multi-layered porous material, sealing the sample in suitable test chamber, filling the pores of the sample material with a wetting liquid, such that the liquid/sample surface free energy is less than the gas/sample surface free energy, using a non-reacting gas to apply pressure to one side of the sample sealed in the test chamber, increasing the gas pressure gradually, so as to displace the liquid from the pores, and increase gas flow through the sample, measuring the pressure at which liquid flows from each successive layer of the sample material, and calculating the pore structure using an equation selected from the group consisting of $p=\gamma(dS/dV)$, $D=4\gamma/p$, and $f=-d[100(F_w/F_d)]/d\ D$.

4 Claims, 5 Drawing Sheets

PORE STRUCTURE ANALYSIS OF INDIVIDUAL LAYERS OF MULTI-LAYERED COMPOSITE POROUS MATERIALS

REFERENCE TO RELATED APPLICATIONS

This application claims an invention, which was disclosed in Provisional Application No. 60/265,470, filed Jan. 31, 2001, entitled "PORE STRUCTURE ANALYSIS OF INDIVIDUAL LAYERS OF MULTI-LAYERED COMPOSITE POROUS MATERIALS". The benefit under 35 USC §119 (e) of the U.S. provisional application is hereby claimed, and the aforementioned application is hereby incorporated herein by reference.

BACKGROUND OF THE INVENTION

1. Field of the Invention

The invention pertains to the field of porous media. More particularly, the invention pertains to a method of measuring the pore structure of the individual layers in multi-layered composite porous materials.

2. Description of Related Art

Multi-layered porous materials and functionally graded porous materials with gradually changing pore structure are being increasingly used for high technology applications. The effectiveness of such materials depends upon the pore structure of individual layers, however, currently available techniques are incapable of providing a measurement of the pore structure of individual layers of a multi-layered composite material. For example, porosimetry only measures the pore volume and pore volume distribution of the entire composite. Moreover, in many of the composite filters, one of the layers is very thin and the low pore volume associated with this layer is not detectable by porosimetry. Flow porometry measures the size of the constricted part of the pores in the entire composite. Unfortunately, the pores in various layers of such composite materials cannot be distinguished using this method, or others taught by the prior art.

A new technique based on the principles of flow porometry has been developed to measure pore structure of individual layers of a composite material. The invention is described below and the analysis of results obtained with a two layered composite filtration medium is presented.

SUMMARY OF THE INVENTION

Pore structures of materials are normally determined by porosimetry or flow porometry, in which the flow occurs parallel to the thickness of the sample. Both of these techniques are incapable of determining the pore structure of individual layers of multi-layered composites. The present invention, based on flow porometry, was developed to measure the pore structure of individual layers. The present invention is described and the pore structures of two individual layers of a composite porous material, as determined by the invention, are presented herein.

Briefly stated, a method of measuring the pore structure of the individual layers in multi-layered composite porous materials includes the steps of providing a sample of a multi-layered porous material, sealing the sample in suitable test chamber, filling the pores of the sample material with a wetting liquid, such that the liquid/sample surface free energy is less than the gas/sample surface free energy, using a non-reacting gas to apply pressure to one side of the sample sealed in the test chamber, increasing the gas pressure gradually, so as to displace the liquid from the pores, and increase gas flow through the sample, measuring the pressure at which liquid flows from each successive layer of the sample material, and calculating the pore structure using an equation selected from the group consisting of $p=\gamma(dS/dV)$, $D=4\gamma/p$, and $f=-d[100(F_w/F_d)]dD$.

DETAILED DESCRIPTION OF THE INVENTION

For testing of a sample material of multi-layered composite porous materials, its pores are filled spontaneously with a wetting liquid for which the liquid/sample surface free energy is less than the gas/sample surface free energy. Pressure of a non-reacting gas is slowly increased on one side of the sample so as to displace the liquid from the pores and increase gas flow through the sample. When the wetting liquid is displaced from the pore, the gas/sample interfacial area increases at the expense of the liquid/sample surface area, and the free energy of the system increases. Gas displaces the liquid, only when the work done by the gas is equal to the increase in surface free energy. Equating the two energy terms, the differential pressure, p required for displacement of a low surface tension wetting liquid at a location in a pore is given by:

$$p=\gamma(dS/dV)$$

where $\gamma$ is the surface tension of the wetting liquid and, dS and dV are the increases in the gas/sample surface area and the volume of gas in the pore respectively (A. K. Jena and K. M. Gupta, Journal of Power Sources, volume 80, 1999, pp. 46–52; Vibhor Gupta and A. K. Jena, Advances in Filtration and Separation Technology, Volume 13b, 1999, pp. 833–844). Diameter of a pore at any location along the length of the pore is defined as the diameter, D of a cylindrical opening such that (dS/dV) of the pore at the location is equal to that of the opening. For a cylindrical opening, (dS/dV) is (4/D). Hence, Equation 1 reduces to:

$$D=4\gamma/p$$

It follows from Equation 2 that pressure required to empty a pore is smallest for the largest pore. Consequently, gas flow rate, which is zero at the beginning, starts at the pressure required to empty the largest pore and increases with increasing pressure because the smaller pores require subsequently more pressure to be emptied.

Figure 1:
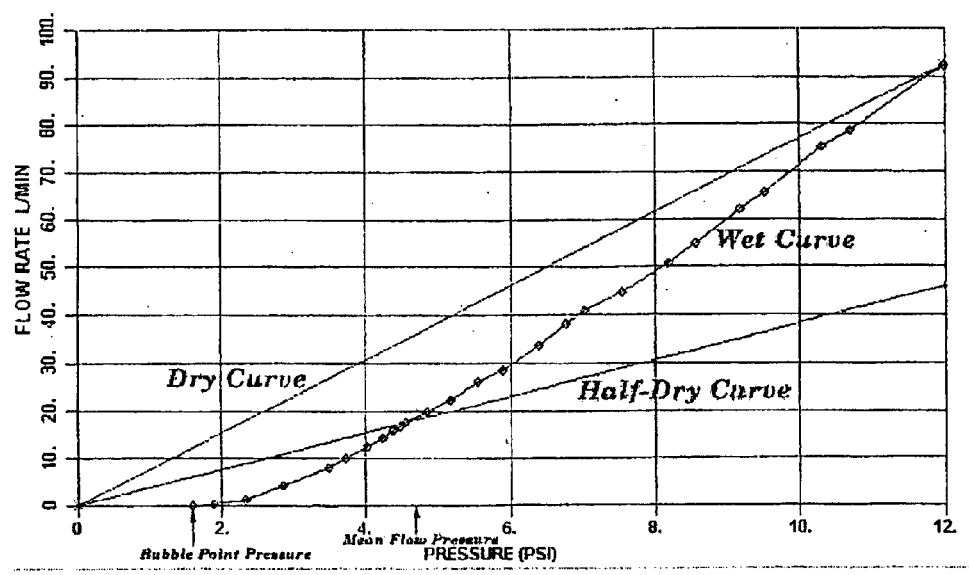
FIG. 1 shows the flow rate of a gas through dry and wet samples as functions of differential gas pressure

Typical results of tests carried out with dry and wet samples are shown in FIG. 1. The figure also shows a half-dry curve that is calculated from the dry curve to yield half of the flow rate through the dry sample at any pressure. The indicated bubble point pressure is the pressure at which the largest pore is emptied, and the flow starts. The pressure at which the half-dry and wet curves intersect is indicated as the mean flow pressure. All of this data is used to determine pore characteristics.

Figure 2:
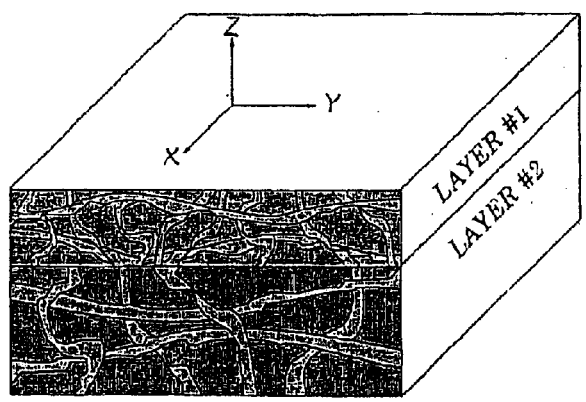
FIG. 2 shows a sketch of a two layer composite.
Figure 3:
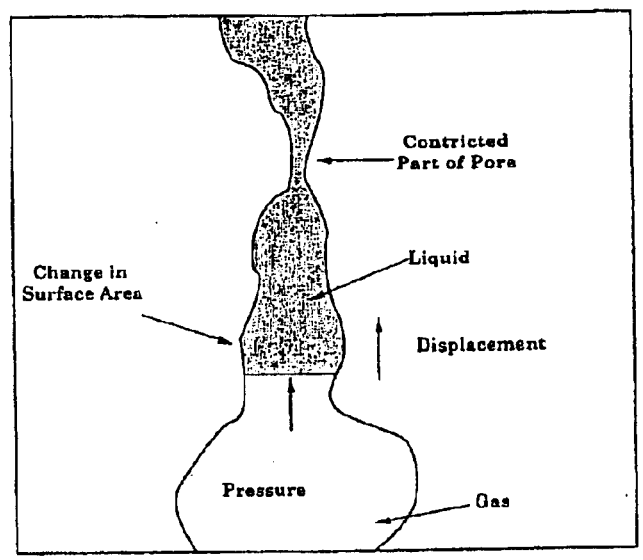
FIG. 3 shows a sketch of a pore, the variation of pore size along its length, and the constricted pore size.

The sketch of the two layered composite used in this study is outlined in FIG. 2. Layer 1 is thin and has small pores. The layer 2 is thick and has large pores. Gas pressure required to empty pores in such a material filled with a wetting liquid is determined by pore size. The pore diameter normally varies along the length of a pore (FIG. 3). Hence, the pressure required to displace the liquid (Equation 2) varies with location along the length of the pore and is a maximum at the most constricted part of the pore (FIG. 3). The pore will be completely emptied, gas flow will occur and the presence of the pore will be detected by flow porometry only when the pressure is equal to this maximum pressure. Thus, flow porometry measures the diameter of the constricted part of the pore.

This basic principle is utilized to determine the pore structures of the two layers of the composite (FIG. 2). The pores are filled with a wetting liquid and gas pressure under layer 2 is increased. If gas is allowed to flow in the z-direction, flow porometry measures the size of the constricted pores that are present in layer 1. On the other hand, if gas is allowed to flow in the x-y plane, flow porometry measures the large pores in layer 2. At higher pressures, the pore structure of layer 1 is also measured. Thus, pore structures of both layers can be separately determined.

Figure 4:
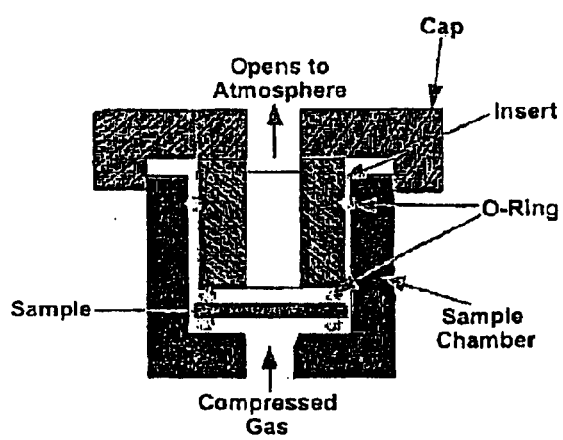
FIG. 4 shows the arrangement for flow in the z-direction.
Figure 5:
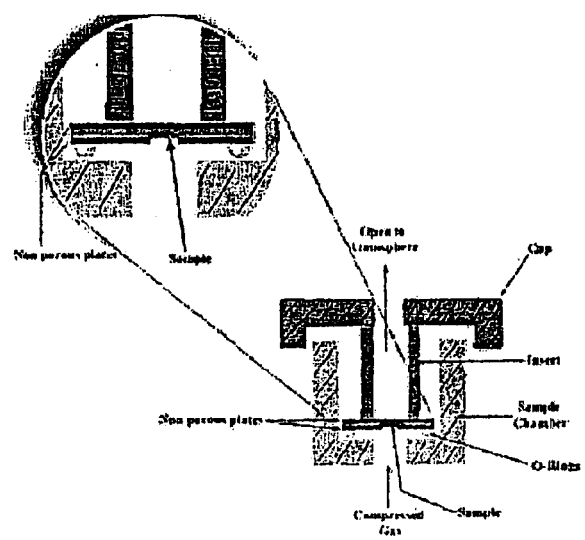
FIG. 5 shows the arrangement for flow along the x-y directions.
Figure 6:
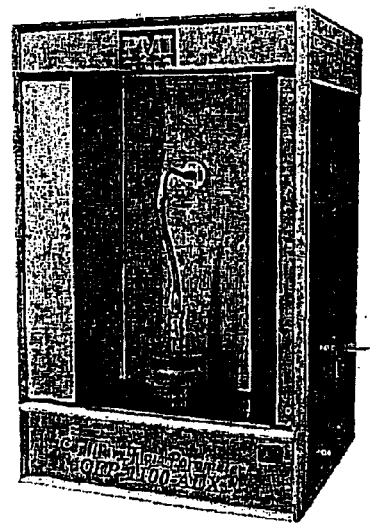
FIG. 6 shows the PMI flow porometer used in this study.

FIG. 4 shows the arrangement for flow in the z-direction and FIG. 5 shows the arrangement for flow along the x-y directions. FIG. 6 shows the PMI flow porometer used in this study. This instrument, with state-of-the-art components, many innovative design features and complete automation is capable of giving highly accurate and reproducible data.

Pore Structure of Layer 1

Figure 7:
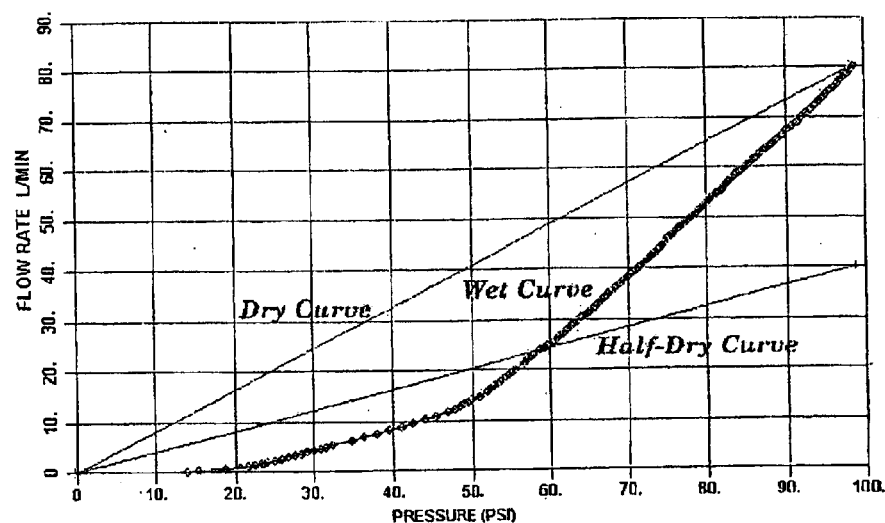
FIG. 7 shows flow rates for flow along the z-direction.

Layer 1 had smaller pores. In order to find its pore structure, a sample saturated with silwick ($\gamma$=20.1 dynes/cm) was placed between two o-rings in the sample chamber (FIG. 4) and pressure of air under layer 2 was slowly increased. The air flowed only along the z-direction and escaped because the o-rings prevented the gas from flowing in the x & y directions. The flow rates are shown in FIG. 7. The largest pore diameter was calculated from the bubble point pressure. The mean flow pore diameter was calculated from the mean flow pressure. The mean flow pore diameter showed that half of the flow through the sample is through pores larger than the mean flow pore diameter.

The pore diameters are listed in Table 1.

Figure 8:
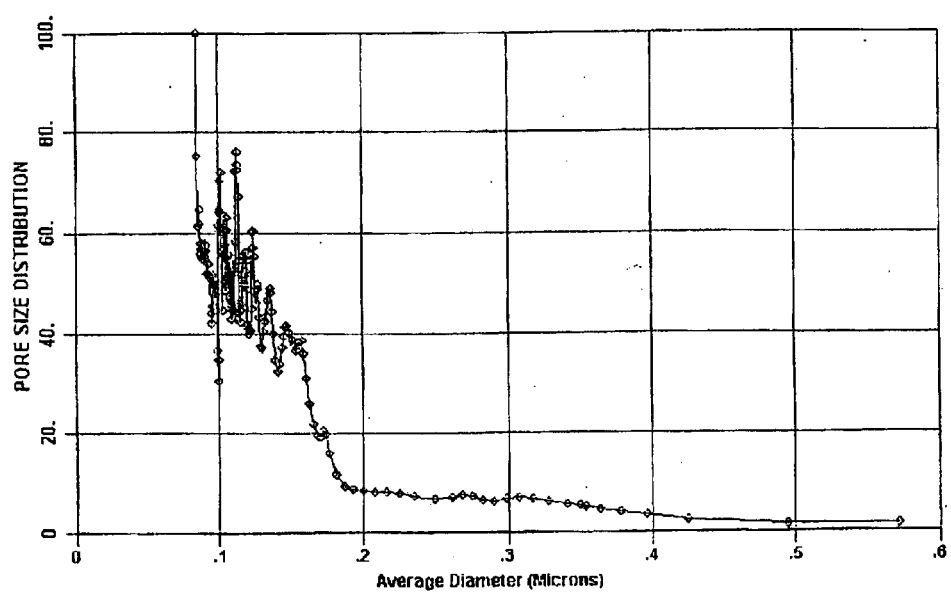
FIG. 8 shows pore size distribution in layer 1.

The pore size distribution function, f is defined as:

$$f = -d[100(F_w/F_d)]/d\,D$$

where $F_w$ & $F_d$ are flow rates through the wet and dry runs at the same differential pressure respectively. The leading negative sign on the right hand side of the equation is due to the fact that ($F_w/F_d$) increases with decrease in pore diameter. The pore distribution is presented in FIG. 8. The area under the curve in any size range gives the percentage flow in that range.

The amount of flow is determined by pore diameter and pore size. The pore distribution suggests that most of the pores are in the range of about 0.4–0.1 microns.

TABLE 1

| | Pore diameters | |
| | Diameter, microns | |
| Layer | The largest pore | The mean flow pore |
|---|---|---|
| Layer 1 | 0.597 | 0.142 |
| Layer 2 | 28.166 | 4.455 |

Pore Structure of Layer 2

Layer 2 had large pores. In order to analyze the pore structure, the sample was soaked in silwick, sandwiched between two non-porous plates and loaded in the sample chamber (FIG. 5). A small central hole in the bottom plate (next to layer 2) allowed entry of gas to the sample. The gas could not escape in the z-direction because of the non-porous top plate, but could escape to the atmosphere by flowing in the x & y directions in the sample.

The flow rates through the wet and dry samples for flow in x & y directions are shown in FIG. 1. The largest pore diameter and the mean flow diameter are listed in Table 1. As expected the pore diameters in layer 2 are much larger than those in layer 1.

Figure 9:
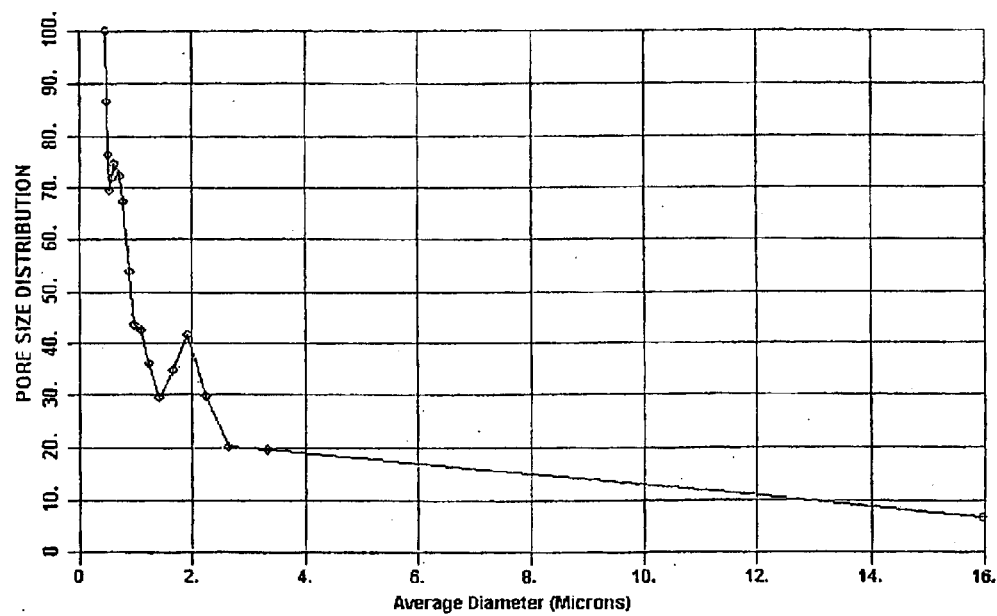
FIG. 9 shows pore distribution for flow in x & y directions.

The pore distribution for flow through x & y directions are shown in FIG. 9. A group of large pores in the size range of about 0.5 to 3 microns is observed. When gas pressure is increased, the large radial pores in layer 2 open up at low pressures. When the pressure is increased and is high enough the small radial pores in layer 1 can also open up. Thus, one can see both groups of pores in layer 2 and layer 1.

Mercury Porosimetry

The composite was also examined by mercury intrusion porosimetry. The results simply showed the pore volume of layer 2. No indication of the pore volume of layer 1 was obtained.

Conclusions

The present invention shows a novel method based on flow porometry that determines the pore structure of individual layers of multi-layered composites. An example of how this method is carried out on a composite was shown with a two-layered composite filtration medium. The characteristics determined by this method are the largest pore diameter, the mean flow pore diameter, and the pore size distribution of each layer were determined. The prior art use of mercury porosimetry could not determine any of the above identified properties.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of determining the pore structure of the individual layers in a multi-layered composite porous material, comprising the steps of:
   a) providing a sample of a multi-layered porous material;
   b) seal said sample in suitable test chamber;
   c) filling pores of said sample with a wetting liquid, such that a liquid/sample surface free energy is less than a gas/sample surface free energy;
   d) using a non-reacting gas to apply pressure to one side of said sample sealed in said test chamber;
   e) increasing said gas pressure gradually, so as to displace said liquid from said pores, and increase gas flow through said sample;

f) measuring said pressure at which liquid flows from each successive layer of said test material; and
g) calculating pore structure using an equation selected from the group consisting of:
   i) $p = \gamma(dS/dV)$;
   ii) $D = 4\gamma/p$; and
   iii) $f = -d[100(F_w/F_d)]/dD$.

2. The method of claim 1, wherein said equation $p = \gamma(dS/dV)$ is used to determine the differential pressure required for displacement of a low surface tension wetting liquid at a location in a pore.

3. The method of claim 1, wherein said equation $D = 4\gamma/p$ is used to determine the pressure required to displace the liquid at various locations along the length of the pore.

4. The method of claim 1, wherein said equation $f = -d[100(F_w/F_d)]/dD$ is used to determine the pore size distribution of each layer of a composite.

* * * * *